(12) United States Patent
Pauly

(10) Patent No.: US 6,500,470 B1
(45) Date of Patent: Dec. 31, 2002

(54) USE OF AT LEAST ONE PROTEIN EXTRACT OF THE MORINGA GENUS PLANT SEEDS AND CORRESPONDING COSMETIC AND/OR PHARMACOLOGICAL COMPOSITION

(75) Inventor: Gilles Pauly, Nancy (FR)

(73) Assignee: Laboratoires Serobiologiques (Societe Anonyme), Pulnoy (FR)

( * ) Notice: Subject to any disclaimer, the term of this patent is extended or adjusted under 35 U.S.C. 154(b) by 0 days.

(21) Appl. No.: 09/646,961

(22) PCT Filed: Feb. 19, 1999

(86) PCT No.: PCT/FR99/00384

§ 371 (c)(1),
(2), (4) Date: Sep. 25, 2000

(87) PCT Pub. No.: WO99/48512

PCT Pub. Date: Sep. 30, 1999

(30) Foreign Application Priority Data

Mar. 24, 1998 (FR) .............................. 98 03787

(51) Int. Cl.⁷ .............................. A61K 6/00; A61K 7/00
(52) U.S. Cl. ....................................... 424/776; 424/401
(58) Field of Search .............................. 424/401, 195.1, 424/725, 776

(56) References Cited

U.S. PATENT DOCUMENTS

| | | | | |
|---|---|---|---|---|
| 4,504,644 A | * | 3/1985 | Lang et al. | 527/201 |
| 5,192,332 A | * | 3/1993 | Lang et al. | 8/405 |
| 5,672,301 A | * | 9/1997 | Orly et al. | 264/4.1 |
| 5,683,683 A | * | 11/1997 | Scafidi | 424/70.19 |
| 5,876,729 A | * | 3/1999 | Pauly | 424/195.1 |
| 5,985,338 A | * | 11/1999 | Suh et al. | 426/69 |
| 6,217,876 B1 | * | 4/2001 | Pauly | 424/195.1 |
| 6,261,662 B1 | * | 7/2001 | Koguchi et al. | 426/540 |

FOREIGN PATENT DOCUMENTS

| | | | |
|---|---|---|---|
| JP | 2989729 | * | 11/1994 |
| JP | 07006423 | * | 11/1995 |
| JP | 07304685 | * | 11/1995 |
| JP | 11116492 | * | 7/1997 |
| JP | 2989729 | * | 12/1999 |
| JP | 11032873 | * | 8/2000 |
| WO | 9837863 | * | 9/1998 |

OTHER PUBLICATIONS

By Le Phac, "Behen Oil: A Classical Oil for Modern Cosmetics", Cosmet Toiletries, 1996, 111(1), 77–80.*

By Rico Magda, "Moringa: A Health–Giving, Water–Purifying Vegetable", *Food Marketing & Technology*, vol. 8, No. 6, Dec. 1994, pp. 10–11.

By U. Eilert et al., "The Antibiotic Principle of Seeds of Moringa oleifera and Moringa stenopetala", *Journal of Medicinal Plant Research*, vol. 42, No. 1, May 1981, pp. 55–61.

* cited by examiner

Primary Examiner—Dameron L. Jones
Assistant Examiner—Lauren Q. Wells
(74) Attorney, Agent, or Firm—Young & Thompson (57) ABSTRACT

The invention concerns the use of at least one protein extract of the Moringa genus plant seeds and a cosmetic and/or pharmaceutical composition containing at least one such extract. More particularly, the invention concerns the use of a protein extract of the Moringa genus plant seeds belonging to the Moringaceae family, as active principle, on its own or combined with at least another active principle, for preparing a cosmetic and/or pharmaceutical composition for topical use on the skin and/or skin appendages.

1 Claim, 7 Drawing Sheets

▨ Desorption : high ionic force

▩ Desorption : high temperature

Extract 1    Extract 3

Standard    Extract 4

USE OF AT LEAST ONE PROTEIN EXTRACT OF THE MORINGA GENUS PLANT SEEDS AND CORRESPONDING COSMETIC AND/OR PHARMACOLOGICAL COMPOSITION

The present invention relates to the field of cosmetology and dermatology, more particularly cosmetics for the care of the skin and nails and hair, and has for its object the use, for cosmetic, dermatologic and/or pharmaceutical applications, of at least one proteic extract of seeds of a plant of the genus Moringa, as well as a cosmetic and/or pharmaceutical composition containing at least one such extract.

The genus Moringa comprises some 14 species of plants (of which particularly *Moringa peregrina, M. aptera, M. concanensis, M. drouhardii, M. hildebrandtii, M. longituba*), among which *Moringa pterygosperma* (synonym: *Moringa oleifera*) is the best known.

It is a tree that grows rapidly and which adapts very well to variable conditions, spread throughout the tropics, in Asia, Africa and South America. The fruits are 30 to 50 cm long, hanging like drumsticks, from which comes the English name "drumstick tree", and its green pods are used as vegetables throughout the world. As a result, the seeds are rarely left to ripen for the production of oil.

The different parts of the tree (leaves, roots, root bark, flowers, seeds) are used in traditional medicine in the countries where it is found.

The seeds of Moringa are characterized by the presence of an oil whose content varies between 21 and 53% according to the species and maturity of the seeds.

For the species *Moringa oleifera*, the contents mentioned in the literature range from 21 to 34%.

The comparison of the oils of the seeds of *Moringa oleifera, Mr. peregrina, M. concanensis* and *M. drouhardii* show a very similar fatty acid content, these oils all having a very high content of oleic acid (71 to 78%) and saturated fatty acids.

Behenic acid ($C_{22}H_{44}O_2$) is the saturated fatty acid typical of Moringa oil (content 2.6 to 4.7%).

Because of its excellent stability against oxidation and its good properties as a perfume fixative, Moringa oil, also called Behen or Ben oil, was in ancient civilizations the oil most used by the producers of unguents for cosmetic and religious uses.

This oil was used by cosmetic formulators until the nineteenth century and its use has been recently "rediscovered".

In addition to their oil content, Moringa seeds have recently claimed the attention of researchers because they are used conventionally for the clarification of water and thus have an economic potential for the treatment and purification of water in developing countries.

It has moreover been shown that the seeds of six species of Moringa that are the most frequent and cultivated contain flocculent compounds.

The compounds responsible for this activity have been isolated and identified: they are compounds of proteic nature (see particularly the articles: "Isolation and characterization of a flocculating protein from *Moringa oleifera* lam", by U. Gassenschmidt, K. D. Jany, B. Tausche and H. R. Niebergall, Biochimica and biophysics acta, 1243:477–481, 1995—"Active agents and mechanism of coagulation of turbid waters using *Moringa oleifera*", of A. Ndabigengesere, K. Subba Narasiah and B. G. Talbot, Water research, 29, 2:703–710, 1995).

From delipidated flour of *Moringa oleifera* seeds, these proteins have been extracted in a buffered aqueous medium, then isolated by cation exchange chromatography.

These flocculent proteins are eluted with an NaCl gradient and are constituted by three active fractions called MO1, MO2, and MO3.

A second chromatographic step permits separating MO2 into three new active fractions called (MO2.1, MO2.2 and MO2.3).

With PAGE electrophoresis under non-denaturing conditions, MO2.1, MO2.2 seem to be homogeneous whilst MO2.3 is constituted by several proteins.

However, with SDS-PAGE, two bands corresponding to the PM 6.5 kDa and 7 kDa are observed for the proteins MO2.1 and MO2.2, which thus would be dimers.

Isoelectrofocalization shows that the isoelectric point of these flocculent proteins is 10.

The amino acid composition of MO2.1 has been determined and shows that this protein contains 60 amino acids with a high content of glutamine (15 residues), arginine (7 residues) and proline (7 residues), the end terminal being blocked by a pyroglutamate function.

The inventors of the present invention have discovered in an unexpected and surprising manner, that the proteic extracts of Moringa seeds, known for their turbid water clarifying properties, also have new and original properties whose beneficial effects on the skin and nails and hair, associated with very high tolerance, renders them directly usable in care cosmetology and in pharmacology, in particular for dermatological applications.

Thus, the principal object of the present invention consists in the use of at least one proteic fraction extracted from seeds of a plant of the genus Moringa belonging to the family of the Moringaceae, as the active principal, alone or in association with at least one other active principal, for the preparation of a cosmetic and/or pharmaceutical composition for topical application for the skin and/or the nails and hair.

The new properties of these proteic extracts flow directly from their particular nature and properties, particularly their basic isoelectric point and their flocculent capacity.

There have particularly been noted an emollient effect, conditioning and hydrating effects because of the great substantivity and chelating effects, rendering them suitable in the field of anti-pollution activity.

According to a preferred embodiment of the invention, the proteic fraction or fractions consist in one or more extracts of the plant *Moringa oleifera*, this or these proteic fraction or fractions containing, based on the dry extract, a protein content comprised between 0.01% and 100% by weight, preferably of about 45% by weight.

Preferably, the proteic fraction or fractions is or are extracted with water or an aqueous solution, particularly saline solutions at different pHs, as the case may be by means of an ultrasonic generator.

Thus, the proteic fraction or fractions is or are constituted by one or more aqueous extracts, saline medium extracts with different pHs, or a buffered medium of whole or decorticated seeds, partially or totally delipitized, by a proteic concentrate, by purified proteins or by a mixture of at least two of the mentioned constituents and having an isoelectric point greater than 7, preferably comprised between 8 and 12.

The proteic fraction or fractions utilized as active principal are preferably obtained by:
  precipitation at the isoelectric point at a pH comprised between 8 and 12
  ion exchange chromatography.
  an extraction process selected from the group formed by affinity chromatography, gel filtration, ultrafiltration, solvent precipitation, of salts such as ammonium sulfate or the like or else by precipitation with the aid of organic polymers or by temperature variation.

Moreover, it has been determined that, in the case of precipitation at the isoelectric point, obtaining the proteic fraction or fractions is promoted by a temperature below ambient temperature, particularly by a temperature of about +4° C.

By way of illustrative and non-limiting examples, there will be described hereafter different processes for obtaining and preparing extracts of seeds of proteic fractions of Moringa seeds, usable in the framework of the present invention.

EXAMPLE 1

Preparation of Extract 1

Kernels of *Moringa oleifera* obtained after decorticating seeds and containing 33.4% (weight/weight) of oil, are delipidated by two successive extractions with refluxing in hexane and, after filtration, the flour is oven-dried at 40° C. and has a residual oil content of 2.5%.

In a reactor there is added 200 g of delipidated flour to 2 liters of distilled water.

After 10 minutes of agitation, the pH is adjusted to 7.5 by addition of 4N NaOH and the extraction is then carried out for one hour at ambient temperature while maintaining the pH at 7.5.

Insolubles are eliminated by centrifugation for 15 minutes at 5000 g.

The supernatant is corrected and then filtered at 0.45 $\mu$m: there is thus obtained 1.77 liter of filtrate of yellow color, containing 4.69% of dry extract and having a concentration of proteins measured by the Biuret method, of 21.54 g/l (namely a proteic purity on a dry extract basis of 20 45.92%).

The extract is dehydrated by spraying and 65.72 grams of material are obtained, having a protein content estimated at 54.7% (N×6.25).

Figure 1:
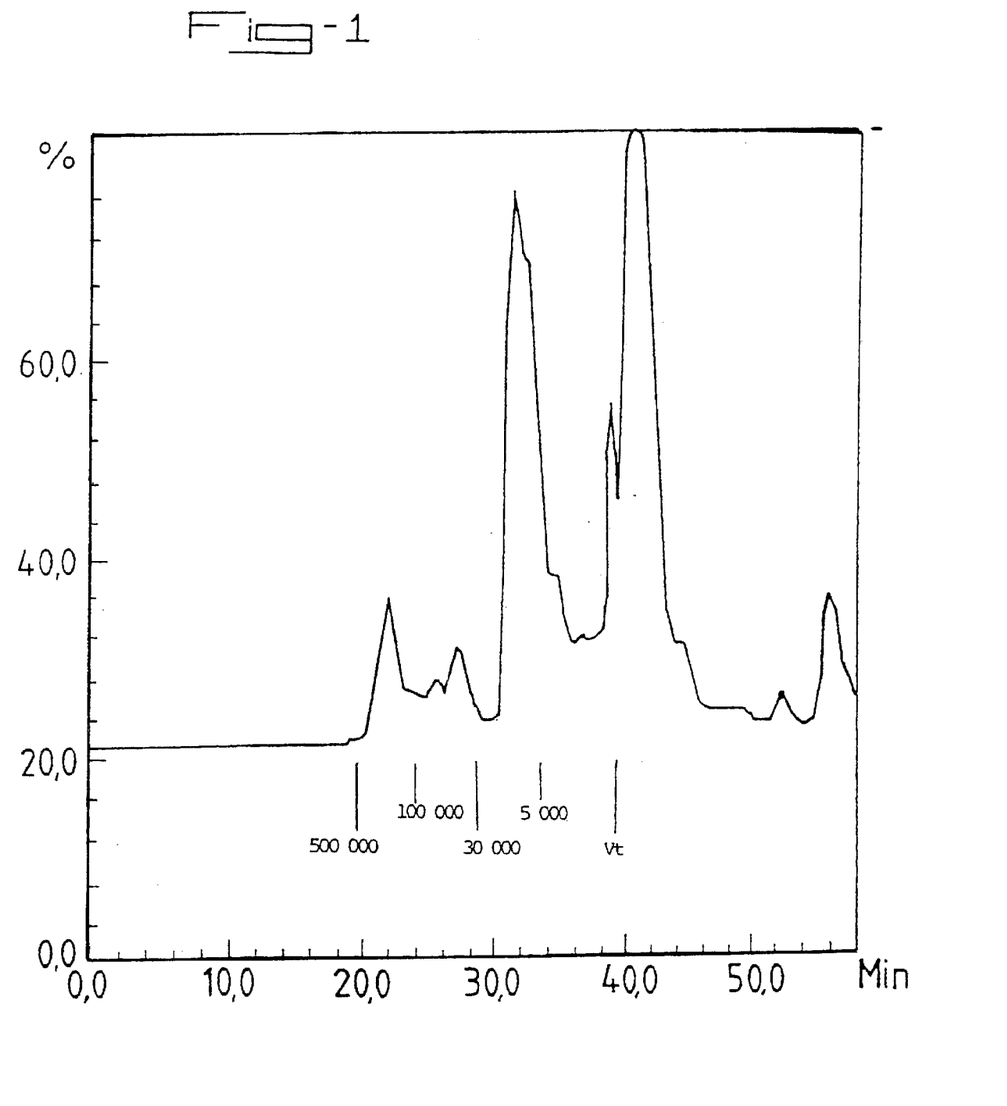
FIGS. 1–3 are chromatographic profiles resulting from analysis by gel permeation of the extracts obtained in Examples 1, 2, and 4, respectively.

Taking account of the eluted peaks between the excluded volume and the total volume of the column, the chromatographic profile resulting from analysis by gel permeation on a Superose column 12HR of this extract (see FIG. 1 of the accompanying drawings) shows a major fraction which represents 52% of the surface and which corresponds to molecular weights between 7,800 and 11,000 Da. The presence of shoulders on the peak confirms the existence of several compounds and the range of molecular weights is near that given in the literature for monomers (6,500 and 7,000 Da) and dimers (13,000 Da) of flocculent proteins of Moringa.

EXAMPLE 2

Preparation of Extract 2

300g of flour delipidized according to Example 1 are extracted so as to obtain a crude aqueous extract.

The pH of the filtrate (2.74 liters) is adjusted to 11.8 by progressive addition of 4N NaOH.

Precipitation begins at about pH 8.0 (turbidity point of the solution) and after 30 minutes the solution is centrifuged for 15 minutes at 5,000 g.

The precipitated binder is collected (43.2 g moist) then washed twice with 500ml of distilled water at pH 11.8.

The precipitate is then dissolved in 270 ml of distilled water (namely 10% of the initial volume) and the pH of the solution is adjusted continuously to 4.5 by 6N HCl so as to permit the solubilization of the precipitate (the dispersion is facilitated by use of an apparatus known by the designation Turax).

After 30 minutes of agitation, the mixture is centrifuged for 15 minutes at 5000 g to eliminate insolubles and the supernatant is filter on a Buchner provided with a Whatman filter No. 41.

There is thus obtained 260 ml of concentrated proteic, yellow and clear, which is dehydrated by lyophilization.

In this way, 11.5 grams of lyophilizate are obtained with a weight content of protein of 90–95%.

Figure 2:
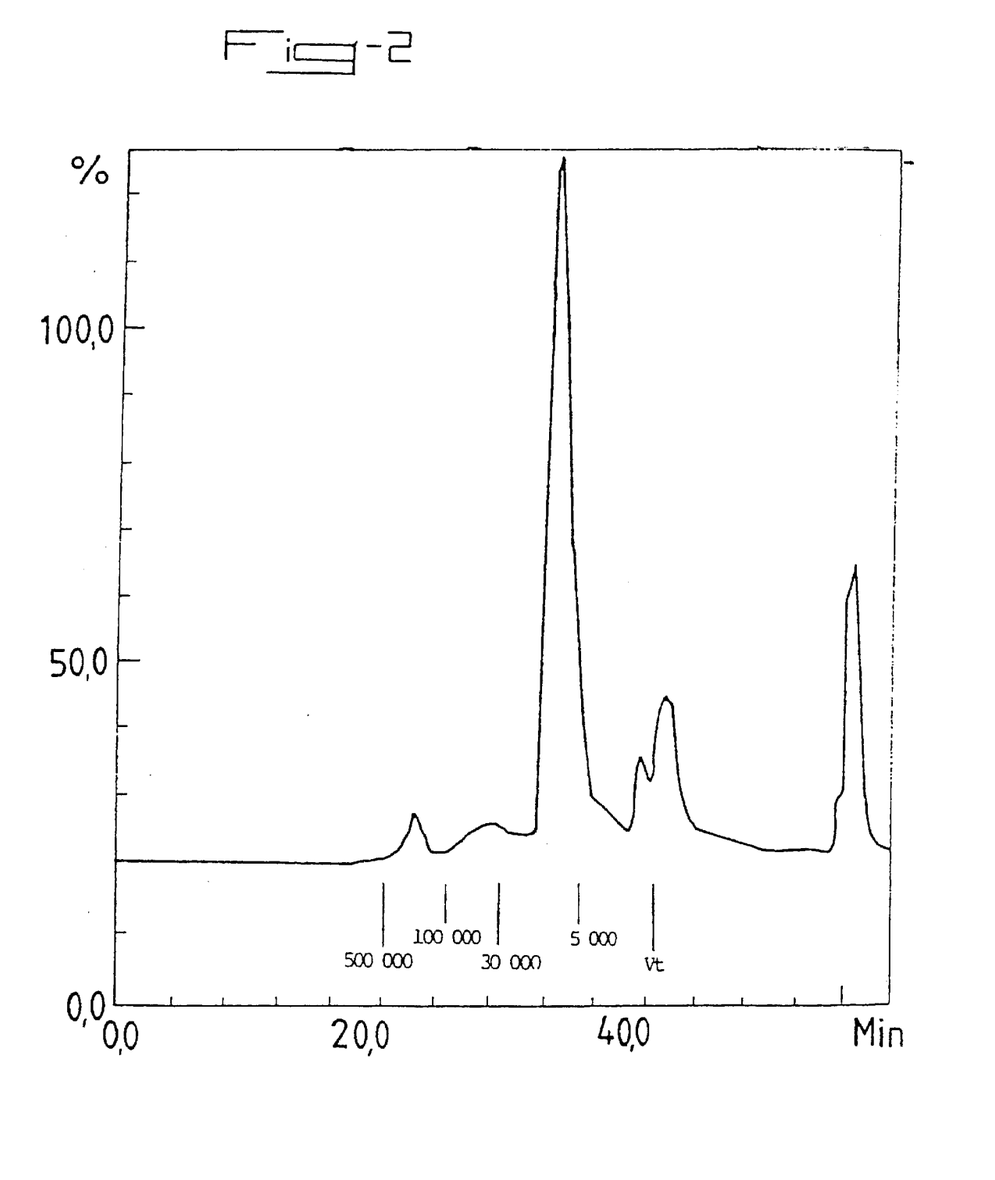

Analysis by gel permeation on a Superose column 12HR of this extract (see FIG. 2 of the accompanying drawings) shows a major fraction which represents 70% of the surface and which corresponds to molecular weights of about 8,800 Da.

EXAMPLE 3

Preparation of Extract 3

Oil of kernels obtained by decortication of the seeds of *Moringa oleifera* is extracted by pressure in a press of a type known as KOMET and the oil cake obtained is crushed so as to obtain a homogeneous flour.

A crude extract is prepared from 1.24 kg of oil cake according to the manner of operation described in Examples 1 and 2.

The proteins are precipitated at pH 11.8 according to Example 2, but a supplementary decantation step for one night at +40° C. is introduced so as to permit better precipitation of the proteins.

The precipitate is treated under the same conditions as in Example 2 (the pH of the solution for reconstituting the precipitate being however 6 instead of 4.5).

The proteic concentrate thus obtained (1.05 liter with 4.59% of dry extract) is dehydrated by spraying and 34.6 grams of the dried material are collected, which is a yield by spraying on the basis of the dry extract of 71.5%.

The protein content on the basis of measuring the nitrogen (N×6.25) is greater than 90% (about 95%).

EXAMPLE 4

Preparation of Extract 4

A crude extract is prepared from 150g of oil cake according to the procedure described in Examples 1, 2 and 3.

After filtration at 0.5 μm, there is obtained 1.35 liter of clear yellow filtrate.

100 grams of carboxymethylcellulose (CM52, WHATMAN) are placed in equilibrium for 30 minutes in 500 ml of distilled water at pH 7.5.

The mixture is filtered on a Buchner provided with a WHATMAN filter No. 42, then the cellulose is collected and equilibrated again in 500 ml of water at pH 7.5.

After elimination of the aqueous medium by filtration, the cellulose is contacted with agitation for one hour at ambient temperature, with the aqueous extract of oil cake of kernels of *Moringa oleifera*.

Figure 3:
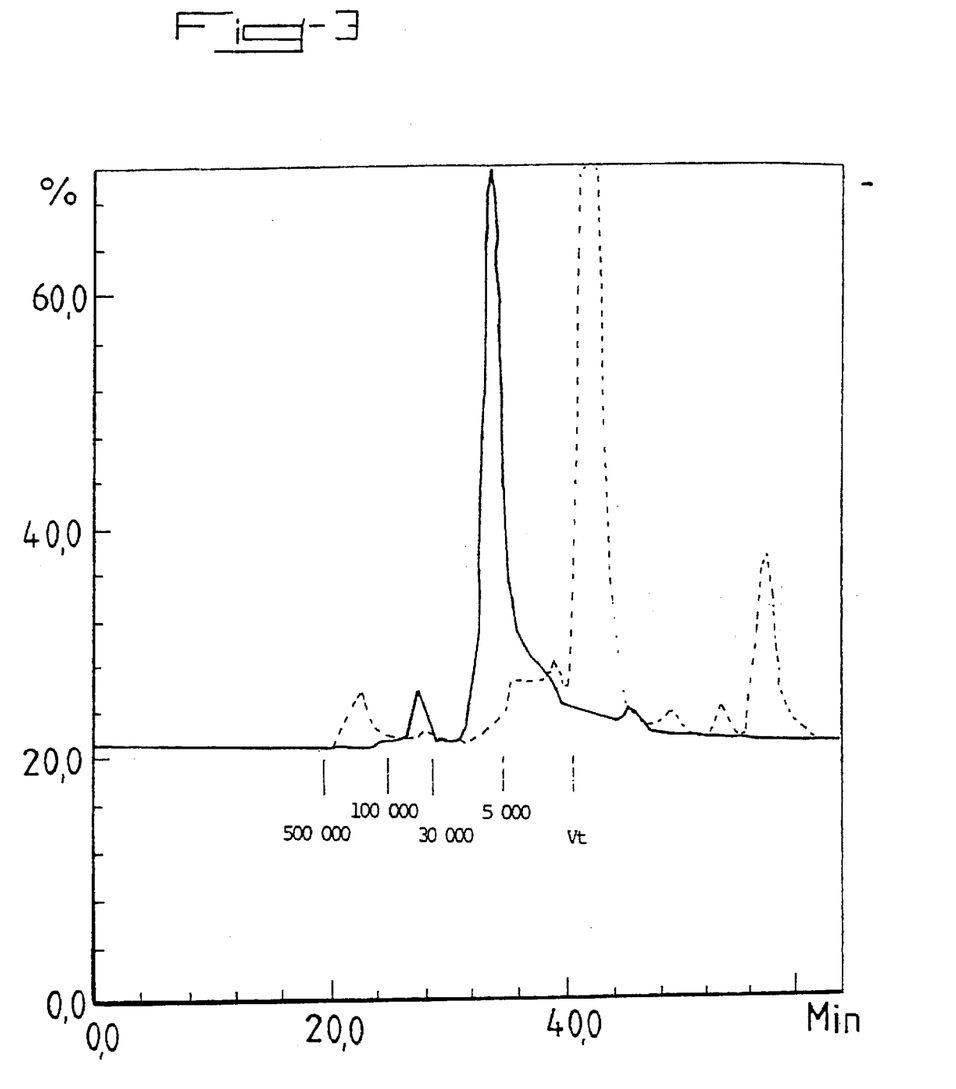

The non-adsorbed compounds (fractions whose chromatographic profile is represented in broken lines in FIG. 3) are eliminated by Buchner filtration and the "loaded" cellulose is then washed twice with one liter of distilled water at pH 7.5 and then Buchner filtered.

The cellulose is then contacted with 120 ml of a solution of NaCl 60g/l, pH 7.5, for 30 minutes.

The proteins eluted in the NaCl medium are recovered by Buchner filtration (the chromatographic profile of the proteins adsorbed on CM 52 and eluted in 60 g/l NaCl, is shown in full line in FIG. 3).

There is thus obtained 110 ml of filtrate with a dry extract content of 9.63% and with a protein concentration of 64.6 g/l (which is to say a protein purity of 67% on the basis of the dry extract).

Analysis by gel permeation on a Superose column 12HR of this extract (see FIG. 3) shows a major fraction which represents 70% of the surface and which corresponds to molecular weights of about 7,100 Da.

The solution can be desalinated by dialysis, or by ultra-filtration and dehydrated by lyophilization, spraying or any other suitable means.

The activities and advantages of the products prepared according to the invention will become clearly apparent in the light of the explanatory description of the tests carried out by the inventors and given hereafter simply by way of illustration and not limitation.

The substantive effect of the proteic fractions of Moringa seeds prepared according to the preceding examples (Extracts 1, 3 and 4) has been evaluated by the desorption test on undamaged natural human hairs and on hairs damaged by permanent waving.

The protocol of the evaluation of adsorption of a substantive agent on the keratin of hair is based on the analysis of the desorbed substance under specific conditions.

The substantive protein of peptidic nature has been extracted from hair under two different conditions:

high temperature (50° C., 1 hour)
high ionic force (0.5 M NaCl, 16 hours),
and measured in extraction liquids after reaction with fluorescamine (reaction with primary amines) by the spectrofluorimetric method (Teglia et al., 1992). The reaction with fluorescamine was carried out in a borate buffer at pH 8 for Extract 1 and at pH 6 for Extracts 3 and 4.

Figure 4A:
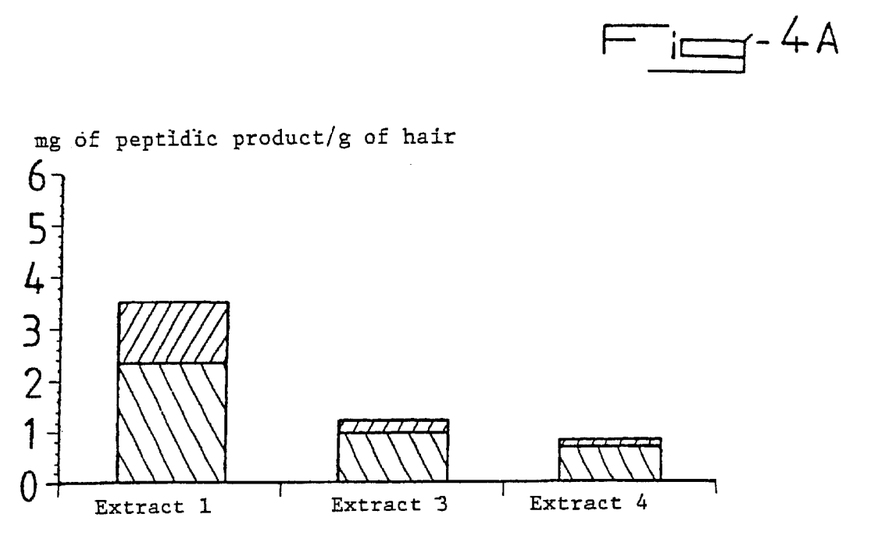
FIGS. 4A and 4B show respectively, for undamaged specimen hair and for hair damaged by permanent waving, the effects of the extracts of the present invention.
Figure 4B:
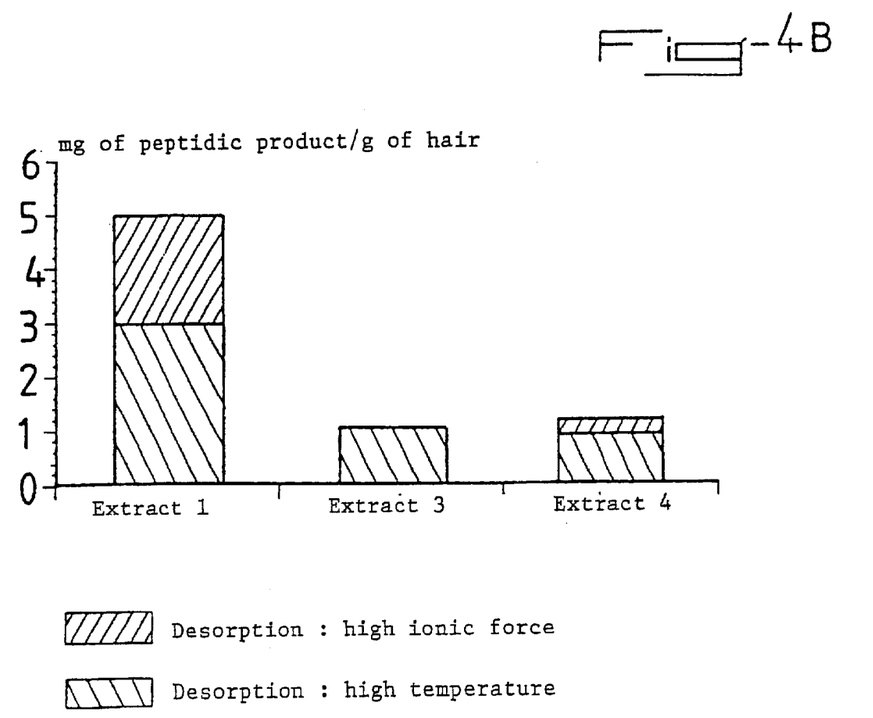

The results are given in Table I hereafter and in the accompanying FIGS. 4A and 4B which show, respectively for undamaged specimen hair (FIG. 4A) and for hair damaged by permanent waving (FIG. 4B), the substantive effect of Extracts 1, 3 and 4 applied to strands of human hair at a concentration of 2% (evaluation by desorption).

TABLE I

| Extracts | Undamaged natural hair | Hair damaged by permanent waving |
| --- | --- | --- |
| 1 | 3.53 mg/g hair | 4.81 mg/g hair |
| 3 | 1.24 mg/g hair | 1.02 mg/g hair |
| 4 | 0.84 mg/g hair | 1.21 mg/g hair |

The substantive effect on the corneal layer of the proteic fractions of Moringa seeds has been evaluated on the dehydration model of the corneal layer in vitro (Obata and Tagami, 1990).

The evaluation protocol consisting in treating squares of isolated corneal layer of human skin, either with solutions of 2% of substantive protein (Extracts 1, 3 and 4), or by distilled water as a standard.

After standing rinsing and drying, the corneal layer is mounted on an in vitro cutaneous hydratation evaluation model for measurement of its dielectric conductivity.

After measuring the dielectric conductivity from a condition of controlled humidity HR=44%, the corneal layer has been humidified in a standard way and measurements of conductivity have been carried out 1, 2, 4, 6 and 24 hours after application of the distilled water.

The corneal layer in the presence of a substantive product is hydrated for a long time (=better retention of water).

Figure 5A:
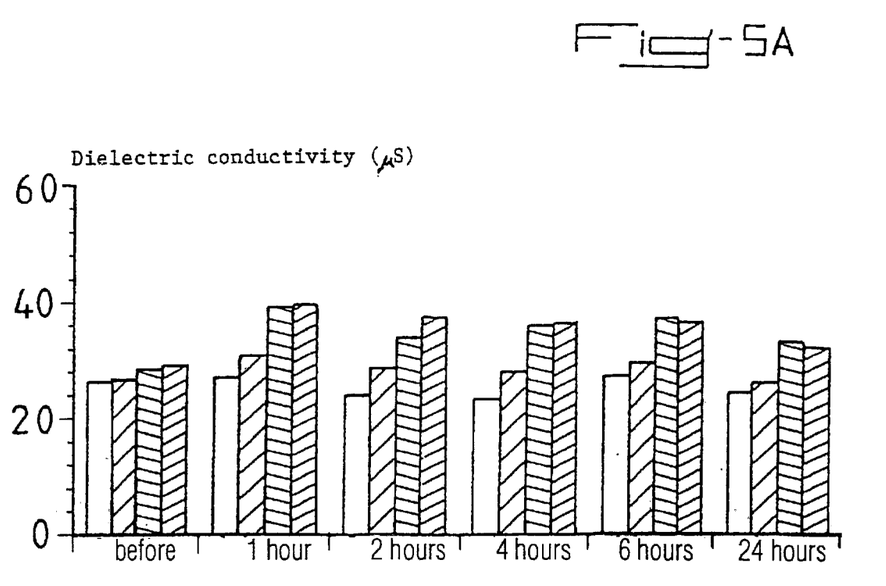
FIGS. 5A and 5B show the results of tests of substantivity of the extracts of the present invention, on the corneal layer evaluated by in vitro cutaneous hydration measurements.
Figure 5B:
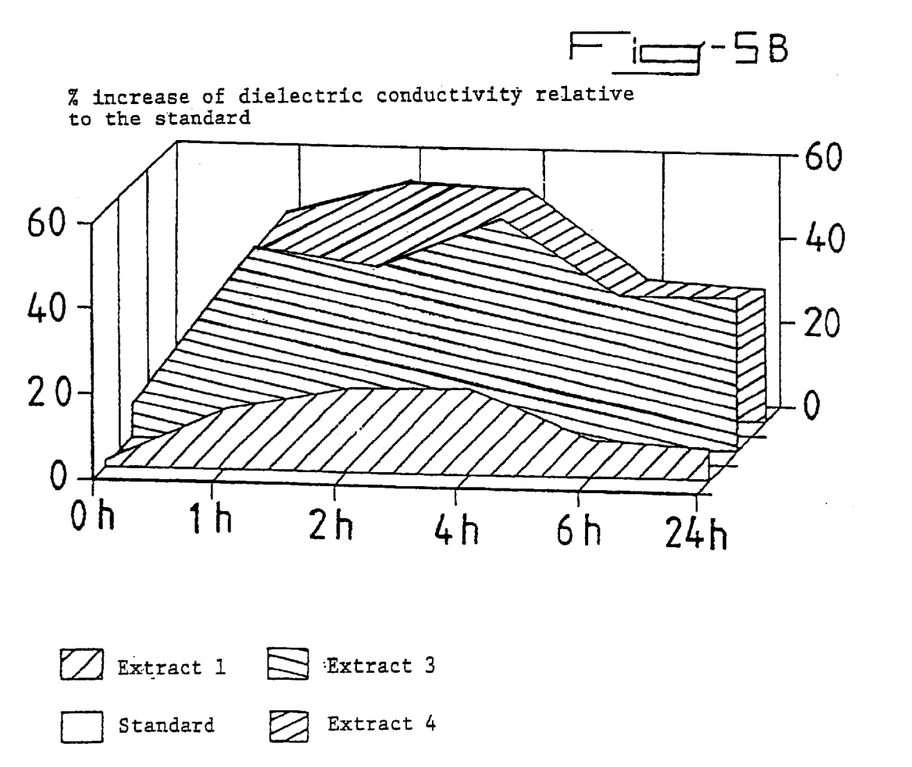

The results relative to the tests of substantivity of Extracts 1, 3 and 4 on the corneal layer evaluated by in vitro cutaneous hydration measurements, are shown in FIGS. 5A and 5B (Mean of 10 tests/+/−SEM/ANOVA at 1 factor/Test a posteriori Fischer).

It will be noted that Extracts 3 and 4 have accentuated and prolonged the hydrating effect of the corneal layer: increase of electrical conductivity of 50% was significant up to 4 hours after application, with a hydrating effect observable to 24 hours after application.

The substantive effect of the proteic fractions of Moringa (Extracts 1, 3 and 4) have been verified in vivo in humans by study of the hydro-retention property of an aqueous solution measured at 1.5% of extract and 1.5% of polyvinyl pyrrolidone sold by the BASF company under the name Kollidon 30 (filmogenic product).

Five cutaneous regions of the antero-internal surface of a forearm were used, for the electrical capacitance measurement of hydration supplied by a compress soaked in purified water, every 30 seconds for 2 minutes. A zone was untreated, the three following being treated first with 4 μl/cm² of an aqueous solution measuring 1.5% of Extract 1, 3 or 4 and 1.5% of Kollidon 30 and the last by 4 μl/cm² of an aqueous solution measuring 1.5% of Kollidon 30 alone.

Figure 6:
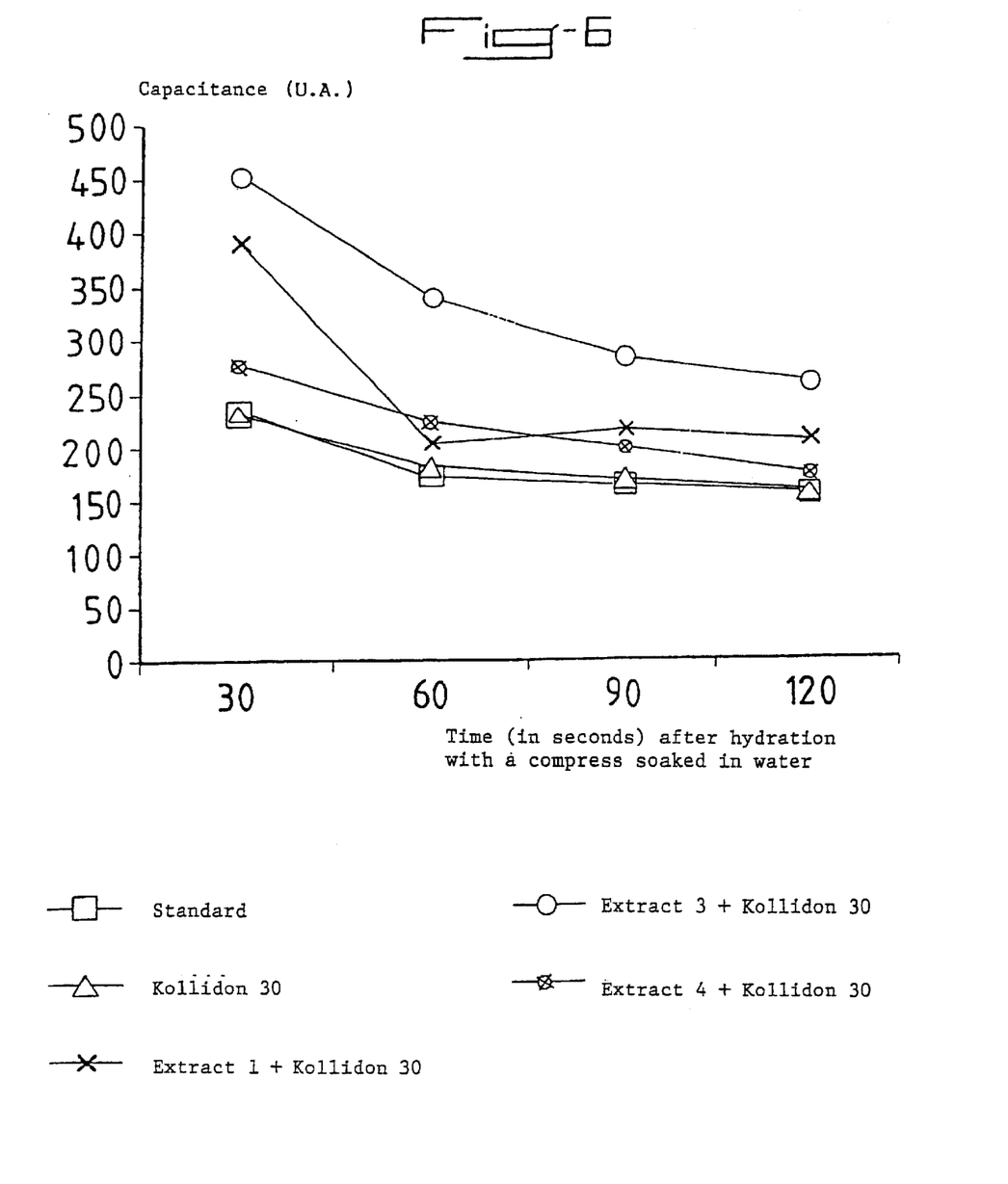
FIG. 6 shows the hydration of the skin when the cutaneous zone is pretreated according to the present invention.

The results shown in FIG. 6 of the accompanying drawings (showing hydro-retention on a subject) show that the hydration of the skin is greater when the cutaneous zone is pre-treated by the mixture of the extract plus Kollidon 30, compared to a untreated reference zone or containing only the filmogen.

The solutions measured at 1.5% extract +1.5% Kollidon 30 therefore have a hydro-retentive activity by substantive effect.

Already known for their clarifying effects on turbid waters, the Moringa proteins have also been shown, in a surprising and unexpected way, to have an anti-pollution effect on human skin by captation of particles such as vegetal carbon.

This clarifying property of the proteic fractions of Moringa seeds has been verified in vitro, by introducing into test tubes, 0.75 ml of an aqueous solution of Extract 1 with 3 ml of aqueous solution of vegetable carbon at 0.5%, compared to 0.25 ml of distilled water but also in contact with 3 ml of the same aqueous carbon suspension.

There has been observed, after one hour of contact, in the tube containing extract 1, that the black suspension of initial carbon had left into place a black precipitate at the bottom of the tube and a water supernatant that is perfectly clear, whilst in the tube without extract, the aqueous suspension of black carbon changed very little.

It has moreover been noted that, in a desirable manner, the addition of a filmogenic compound such as Kollidon 30 (trademark for polyvinylpyrrolidone), further accelerates the process of clarification.

A test in vivo in humans permits the observation that an aqueous solution of polluting vegetable carbon applied to the skin, gave rise to substantial soiling of the surface with penetration of the particles into the superficial levels of the corneal layer.

The effectiveness of Extract 1 as a cutaneous depollutant against the soiling effect of carbon and against penetration of polluting particles into the corneal layer, has also been experimentally evaluated.

The test carried out under standardized conditions consisted in applying to the anterior-internal surface of the forearm a mixture of the extract of Moringa and Kollidon, measured each to be 1.5% in water, in the amount of 4 mg/cm$^2$. This treatment was followed by voluntary pollution of the skin with the same aqueous carbon solution measuring 0.5w. The skin was then rinsed with distilled water without rubbing, the rinsing water being taken up by suction.

Then a "stripping" or coating (with a film support) has been applied to the skin, and then taken off.

Microscopically, at a magnification of 100, there was observed on the one hand the reference stripping of the state of the skin at its surface and, on the other hand, the cutaneous microcontour with the first levels of the corneal layer, after stripping or layering.

Correspondingly, the same pollution was applied to a cutaneous region without preliminary treatment.

Figure 7A:
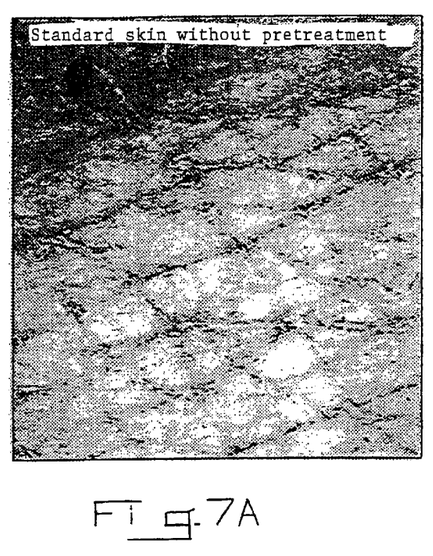
FIGS. 7A and 7B show the penetration of carbon particles into the corneal layer of skin respectively with and without the practice of the present invention.
Figure 7B:
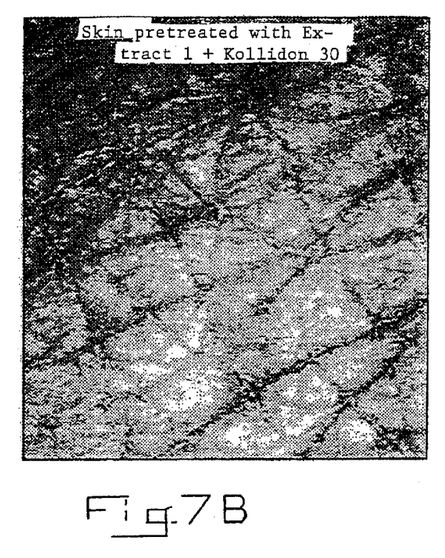

The images of the skin under 100-fold magnification after stripping or layering permitted showing a very great decrease of the penetration of the carbon particles into the corneal layer of the skin pre-treated by the mixture of the extract of Moringa and Kollidon (FIG. 7B) compared to the reference skin (FIG. 7A) for which the penetration was much greater.

Figure 8A:
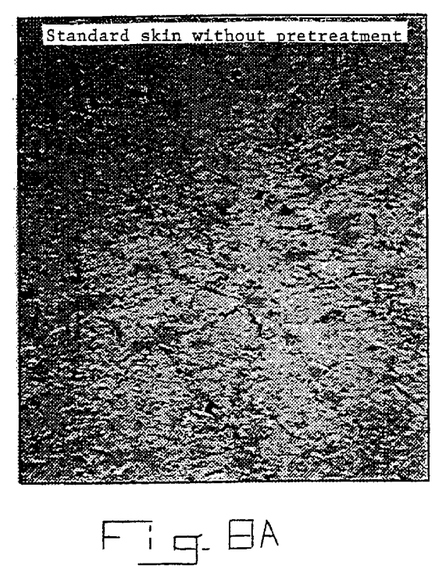
FIGS. 8A and 8B show images of stripping of the skin respectively without and with the practice of the present invention.
Figure 8B:
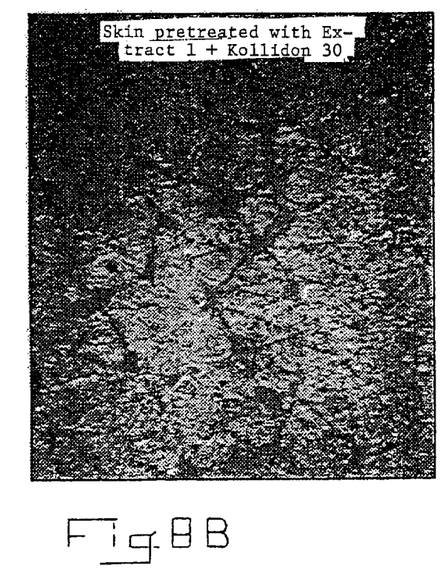

Microscopic images of the strippings carried out on skin pre-treated with a mixture of extract +Kollidon (FIG. 8B) have been a great decrease in the quantity of carbon particles, proving that the same mixture of extract and Kollidon permitted in the course of the rinsing operation a much more efficacious cleaning of the skin. Thus, by comparison with the stripping of the skin previously untreated with extract (FIG. 8A), numerous particles of carbon which were not eliminated by the rinsing operation remained stuck to the stripping material.

The Moringa extract therefore exerts an antipollution activity in two separate and complementary manners:

- it captures the particles of carbon and, in combination with a filmogen, it prevents these latter from penetrating the corneal layer,
- by retaining the carbon particles, it promotes their elimination in the course of a simple rinsing operation.

Extracts according to the above invention can be used not only for applications of health care of the skin (products for the face and the body, day products and night products, solar products, anti-wrinkle hygienic products, anti-pollution products), but also in the field of capillary care and hygiene (lotion or shampoo, creams, foams, protective products, repairing products, emollients and photoprotectors or else products for permanent waving and hair coloring), products for the nails (creams, lotions, lacquers, hydrating agents, filmogens, protectors and repairers) and finally products for the lips (lipsticks, lip rouge, balm, hydrating material, filmogens).

Thus, the present invention also has for its object a cosmetic and/or pharmaceutical composition, particularly for topical use for the skin or the nails or hair, characterized in that it contains, as active principal, alone or associated with at least one other active principal, one or several proteic fractions as described above, with a weight content comprised between 0.01% and 80%, preferably about 2%.

The proteic fractions obtained according to the present invention can be used either in the natural form (natural proteins), without structural modification, or in a modified or functionalized form by any one of the following treatments:

- polymerization by natural proteins extracted from plants of the genus Moringa,
- fermentation by microbial or vegetable cells,
- chemical hydrolysis of the natural proteins extracted from the plant of the genus Moringa,
- enzymatic hydrolysis of the natural proteins by proteins of animal or vegetable, microbial or fungal origin,
- chemical or enzymatic functionalization,
- chemical modification by grafting molecules or compounds such as for example oses, osides, lipids or the like.

They can also be incorporated in or associated with any suitable cosmetic vector such as for example filogenic agents, liposomes, cyclodextrins, micelles, chylomicrons, macro-, micro- and nano-particles as well as macro-, micro-, and nano-capsules, or else be absorbed or grafted on organic polymers or mineral supports.

As a result, it has been determined and shown above that the proteic extract fractions have particularly substantive and hydrating activities for the skin, lips and nails and hair, in particular the epidermis, and particularly the corneal layer and its cutaneous annexes, namely skin, hair and nails, as well as physiological conditioning effects on the skin, lips and nails and hair, restructuring, repairing and hydrating the skin and the nails and hair, anti-wrinkle effects and anti-pollution effects (skin, lips, hair).

By way of non-limiting examples of practical embodiments of the composition according to the invention, there will be described hereafter different products or cosmetic preparations comprising at least one proteic extract of seeds of the plant *Moringa oleifera*.

EXAMPLE 1

A cosmetic product in the form of a hydrating and repairing milk can for example have a weight composition, constituted of the following aqueous and fatty phases, as indicated hereafter.

| | | |
|---|---|---|
| Fatty phase: | Isostearyl and Diglyceryl Succinate | 3.00 |
| | Paraffin oil | 15.00 |
| | Quaternary 18 Hectorite | 0.50 |
| | Poly (PEG-22/Dodecyl Glycol) | 1.00 |
| Aqueous phase: | Magnesium sulfate | 0.80 |
| | Butylene glycol | 4.00 |
| | Protein extract of Moringa oleifera (according to Example 1) and | 1.00 |
| | Distilled water | 9.00 |
| | Elestab 4112 (Laboratoires Sérobiologiques) | 0.35 |
| | Perfume | 0.30 |
| | Distilled water | qsp 100.00 |

The process of preparation of the above hydrating and repairing milk consists essentially in bringing the fatty phase to 80° C., bringing the water of the aqueous phase also to 80°

C. and dissolving in it the preservative (Elestab 4112), then pouring the aqueous phase into the fatty phase with turbine agitation and progressively cooling with agitation, then adding thereto, at about 50C., the mother aqueous solution of proteic extract of Moringa, then the perfume and, finally, continuing agitation until cooling is complete.

EXAMPLE 2

A cosmetic product in the form of a anti-wrinkle repairing cream could, for example, have a weight composition, constituted of the following aqueous and fatty phases, as indicated hereafter.

| Fatty phase: | Ceteareth 25 | 2.00 |
|---|---|---|
| | Ceteareth 6 (and) stearylic Stearyl Alcohol | 1.00 |
| | Cetyl alcohol | 4.00 |
| | Glycerol stearate | 4.00 |
| | Petrolatum | 5.00 |
| | Caprylic/capric triglycerides | 5.00 |
| Aqueous phase: | Glycerin | 10.00 |
| | Proteins of Moringa Oleifera (prepared according to Example 2) and | 1.50 |
| | Distilled water | 8.50 |
| | Preservative Elestab 4112 (Laboratoires Sérobiologiques) | 0.40 |
| | Perfume | 0.30 |
| | Distilled water | qsp 100 |

The process for the production of the above antiwrinkle repairing cream consists essentially in bringing the fatty phase to 80C., bringing the aqueous phase also to 80° C. and dissolving therein the Elestab 4112, separately preparing the mother solution of proteic extract of *Moringa oleifera*, pouring the fatty phase into the aqueous phase with turbine agitation, then, at about 50° C., introducing thereinto the mother solution of extract of Moringa and finally continuing agitation until cool.

EXAMPLE 3

A cosmetic product in the form of a hydrating and anti-pollution day cream could, for example, have a weight composition, constituted from the following aqueous and fatty phases, as indicated hereafter.

| Fatty phase: | Glycerol stearate | 14.00 |
|---|---|---|
| | Octyldodecanol | 6.00 |
| | Dibutyl adipate | 6.00 |
| | Ceteareth 12 | 1.50 |
| | Ceteareth 20 | 1.50 |

-continued

| Aqueous phase: | PVP | 0.50 |
|---|---|---|
| | Glycerin | 4.00 |
| | Elestab 388 (Laboratoires Sérobiologiques) | 2.00 |
| | Proteic extract of Moringa (Extract No. 2) and | 1.00 |
| | Distilled water | 9.00 |
| | Perfume | 0.20 |
| | Distilled water | qsp 100 |

The process for preparation of the above hydrating and anti-pollution day cream consists in bringing the fatty phase to 80° C., bringing the aqueous phase also to 80° C. and dissolving therein the Elestab 388 and PVP, pouring the fatty phase into the aqueous phase with turbine agitation at 80° C., then progressively cooling with agitation and thereafter introducing, at about 50° C., the mother dispersion of Moringa proteins and finally continuing agitation until cool.

EXAMPLE 4

A cosmetic product in the form of an anti-pollution and biofilmogenic reparative unrinsed capillary lotion could for example have a weight composition as indicated hereafter.

| Proteins of Moringa prepared according to Example 4 | 0.50 |
|---|---|
| Distilled water | 9.50 |
| Hydroxyethylcellulose | 0.50 |
| Elestab 305 (Laboratoires Sérobiologiques) | 0.50 |
| Perfume | 0.10 |
| Cremophor RH40 | 0.30 |
| Distilled water | qsp 100.00 |

The process of preparation of the anti-pollution and biofilmogenic reparative unrinsed capillary lotion consists essentially in dissolving Elestab 505 and hydroxyethylcellulose in water heated to about 50° C., dispersing therein the perfume and Cremophar RH40, then bringing the mixture to ambient temperature, and then dissolving therein the proteins of Moringa and finally filtering.

Of course, the invention is not limited to the described embodiments. Modifications remain possible, particularly as to the construction of the various elements or by substitution of technical equivalents, without thereby departing from the scope of protection of the invention.

What is claimed is:

1. A method of hydrating, repairing, producing anti-wrinkle effects and/or producing anti-pollution effects for skin, lips, nails and/or hair of a person, comprising applying a composition to said skin, lips, nails and/or hair of said person, said composition comprising an effective amount of an extract of a plant of the genus Moringa belonging to the family Moringacaea, in admixture with a topically acceptable excipient; the improvement wherein said extract is a protein fraction extracted from seeds of said plant.

* * * * *